United States Patent [19]

Arai et al.

[11] Patent Number: 5,188,969
[45] Date of Patent: Feb. 23, 1993

[54] MONOCLONAL ANTIBODY TO HUMAN LYMPHOTOXIN AND USE THEREOF

[75] Inventors: Kazuhiko Arai, Sagamihara; Akira Fujiwara; Shosaku Motoda, both of Niigata; Hiroyasu Suzuki, Tokyo, all of Japan

[73] Assignee: Denki Kagaku Kogyo Kabushiki Kaisha, Tokyo, Japan

[21] Appl. No.: 366,568

[22] Filed: Jun. 15, 1989

[30] Foreign Application Priority Data

Jun. 20, 1988 [JP] Japan .................................. 63-150021

[51] Int. Cl.⁵ ...................... G01N 33/53; C12N 5/20; C07K 13/00
[52] U.S. Cl. .................. 436/548; 435/240.27; 436/518; 436/824; 530/388.23
[58] Field of Search ............... 436/548, 518, 824; 424/85.1, 88; 435/69.5, 70.21, 240.26, 240.27; 530/387, 388, 413, 809, 388.23; 935/81, 89, 108

[56] References Cited

U.S. PATENT DOCUMENTS

| | | | |
|---|---|---|---|
| 4,833,074 | 5/1989 | Fagerhol et al. | 435/7.33 |
| 4,920,196 | 4/1990 | Aggarwal | 530/351 |
| 4,959,457 | 9/1990 | Bringman | 530/387 |

FOREIGN PATENT DOCUMENTS

| | | |
|---|---|---|
| 0230781-A2 | 8/1987 | European Pat. Off. . |
| 0232107-A2 | 8/1987 | European Pat. Off. . |
| 0297833-A2 | 1/1989 | European Pat. Off. . |
| 335263 | 4/1989 | European Pat. Off. . |
| 3620656.3 | 6/1986 | Fed. Rep. of Germany . |
| 61-56197 | 3/1986 | Japan . |
| 62-181298 | 8/1987 | Japan . |
| 62-258324 | 11/1987 | Japan . |
| 63-5099 | 1/1988 | Japan . |
| 63-8398 | 1/1988 | Japan . |
| 63-8399 | 1/1988 | Japan . |

OTHER PUBLICATIONS

Eisen, in *Immunology*, Harper and Row, Inc., 1974, pp. 409–411.
T. S. Bringman et al. Hybridoma 6, 489(1987).
Y. Kobayashi et al. J. Biochem. 100, 727(1986).
P. W. Gray et al. Nature 312, 721(1984).
A. Meager et al. J. Immunol. Methods, 104, 31(1987).
Journal of Immunology, vol. 10, No. 1, 1989, pp. 93–105, Marcel Kekker, Inc.; H. Tada et al.
European Search Report.

*Primary Examiner*—Esther L. Kepplinger
*Assistant Examiner*—Donna C. Wortman
*Attorney, Agent, or Firm*—Sprung Horn Kramer & Woods

[57] ABSTRACT

A monoclonal antibody reactive with a C-terminal half of human lymphotoxin, and fragments thereof; a hybridoma cell line producing a monoclonal antibody reactive with a C-terminal half of human lymphotoxin; a process for the production of a monoclonal antibody reactive with a C-terminal half of human lymphotoxin, comprising the steps of culturing the above-mentioned hybridoma in a medium to secrete the antibody, and recovering the antibody from the culture supernatant; a process for the production of a monoclonal antibody reactive with a C-terminal half of human lymphotoxin, comprising the steps of inoculating a hybridoma to a mammal, obtaining ascites from the mammal, and recovering the monoclonal antibody from the ascites; a process for the production of a hybridoma cell line producing a monoclonal antibody reactive with a C-terminal half of human lymphotoxin, comprising the step of immunizing a mammal with a conjugate of zinc and a purified recombinant human lymphotoxin, obtaining spleen cells from the immunized mammal, fusing the spleen cells with myeloma cells, and cloning a hybridoma producing the monoclonal antibody; an adsorbent for lymphotoxin comprising a solid carrier and the above-mentioned monoclonal antibody or fragment of the antibody, wherein the monoclonal antibody is bonded to the surface of the solid carrier; a process for the purification of lymphotoxin comprising the steps of placing a material containing lymphotoxin in contact with the above-mentioned adsorbent to adsorb the lymphotoxin to the adsorbent, and eluting the adsorbed lymphotoxin with an eluent; and an assay method or assay kit for lymphotoxin using the above-mentioned monoclonal antibody or fragment thereof.

7 Claims, 2 Drawing Sheets

Fig. 1

```
  1                                          10
MET HIS LEU ALA HIS SER ASN LEU LYS PRO
                                             20
ALA ALA HIS LEU ILE GLY ASP PRO SER LYS
                                             30
GLN ASN SER LEU LEU TRP ARG ALA ASN THR
                                             40
ASP ARG ALA PHE LEU GLN ASP GLY PHE SER
                                             50
LEU SER ASN ASN SER LEU LEU VAL PRO THR
                                             60
SER GLY ILE TYR PHE VAL TYR SER GLN VAL
                                             70     A
VAL PHE SER GLY LYS ALA TYR SER PRO LYS
                                             80
ALA THR SER SER PRO LEU TYR LEU ALA HIS
                                             90
GLU VAL GLN LEU PHE SER SER GLN TYR PRO
                                            100
PHE HIS VAL PRO LEU LEU SER SER GLN LYS
                                            110
MET VAL TYR PRO GLY LEU GLN GLU PRO TRP
                                            120
LEU HIS SER MET TYR HIS GLY ALA ALA PHE
                                            130
GLN LEU THR GLN GLY ASP GLN LEU SER THR
                                            140
HIS THR ASP GLY ILE PRO HIS LEU VAL LEU
                                            150
SER PRO SER THR VAL PHE PHE GLY ALA PHE

ALA LEU
```

Fig. 2

```
  1                                          10
LEU PRO GLY VAL GLY LEU THR PRO SER ALA
                                          20
ALA GLN THR ALA ARG GLN HIS PRO LYS MET
                                          30
HIS LEU ALA HIS SER THR LEU LYS PRO ALA
                                          40
ALA HIS LEU ILE GLY ASP PRO SER LYS GLN
                                          50
ASN SER LEU LEU TRP ARG ALA ASN THR ASP
                                          60
ARG ALA PHE LEU GLN ASP GLY PHE SER LEU
                                          70
SER ASN ASN SER LEU LEU VAL PRO THR SER
                                          80
GLY ILE TYR PHE VAL TYR SER GLN VAL VAL
                                          90
PHE SER GLY LYS ALA TYR SER PRO LYS ALA
                                         100
THR SER SER PRO LEU TYR LEU ALA HIS GLU
                                         110
VAL GLN LEU PHE SER SER GLN TYR PRO PHE
                                         120
HIS VAL PRO LEU LEU SER SER GLN LYS MET
                                         130
VAL TYR PRO GLY LEU GLN GLU PRO TRP LEU
                                         140
HIS SER MET TYR HIS GLY ALA ALA PHE GLN
                                         150
LEU THR GLN GLY ASP GLN LEU SER THR HIS
                                         160
THR ASP GLY ILE PRO HIS LEU VAL LEU SER
                                         170
PRO SER THR VAL PHE PHE GLY ALA PHE ALA

LEU
```

B

MONOCLONAL ANTIBODY TO HUMAN LYMPHOTOXIN AND USE THEREOF

BACKGROUND OF THE INVENTION

1. Field of the Invention

The present invention relates to an anti-human lymphotoxin monoclonal antibody, hybridoma cell lines producing said antibody, a process for purification of human lymphotoxin using said antibody, and an immunological assay method and kit using the antibody.

2. Description of the Related Art

Conventionally, antibodies to a particular antigen are prepared by immunizing an animal with the antigen, obtaining blood from the immunized animal and separating an antiserum from the obtained blood. But since an antiserum comprises a plurality of antibodies with different antigen-specificities, it is very difficult to isolate antibodies with a desired antigen specificity.

Further, the specific antibodies thus obtained react with different antigen-determinants and exhibit heterogeneous affinities to the antigen. In 1975, Köhler and Milstein, Nature, 256, 495–497, disclosed a method of obtaining a hybrid cell (hybridoma) which produces an antigen-specific antibody by a fusion between a mouse myeloma cell and an immunized mouse spleen cell, and since that time a large number of hybridomas producing monoclonal antibodies specific to different antigens have been disclosed. These hybridomas are characterized by producing a monoclonal antibody having a predetermined specificity, and can be cloned and stably cultured, and accordingly, there is no limit to the ability to produce an antibody specific to a single antigen determinant.

In a general procedure for constructing a hybridoma, a material containing an antigen to which an intended monoclonal antibody is directed is repeatedly administered to a mammal such as mouse or rat, and after the presence of the intended antibody in serum taken from the animal is confirmed, the spleen is removed from the animal to prepare a cell suspension. Next, the thus obtained cells are placed in contact with myeloma cells, in the presence of a cell fusion promoter such as polyethylene glycol, to fuse the cells. The thus obtained fused cells are then carefully subjected to repeated screening procedures, to isolate a cell line secreting a monoclonal antibody having a desired specificity.

Lymphotoxin is a lymphokine produced by lymphocytes or established lymphoid cells stimulated with an antigen or mitogen, and is promising as an anticancer drug (Granger, G. A. et al., 14th International Congress of Chemotherapy, Kyoto, Japan, Jun. 23-28, 1985, Abstract p15; E. W. B. Jeffes III et al., Lymphokine Research 6, 141, 1987) due to its cytotoxic property to cancer cells; as an antiviral drug (G. H. W. Wong and D. V. Goeddel, Nature, 323, 819, 1986) due to its toxic property to viruses; and as a macrophage activating drug (Japanese Patent Application No. 62-199144), in the medical field. Moreover, other biological activities such as B lymphocyte growth promoting action (J. K. Kehrl et al, Science, 238, 1144, 1987, and an inhibition of lipoprotein lipase activity (Patton, J. S. et al, Proc. Natl. Acad. Sci. U.S.A., 83, 8313, 1986) have been reported. Considering the importance and advantages gained from these biological activities, there is an urgent need to develop accurate and rapid assay methods and assay reagents.

Lymphotoxin can be produced by gene recombination techniques and has been confirmed to have the same lymphotoxin activities as these of a natural lymphotoxin produced by lymphocytes (P. W Gray et al., Nature, 312, 721, 1984; Japanese unexamined Patent Publication, KOKAI No. 62-151182).

The active site of Lymphotoxin is at the carboxyl terminal (c-terminal) side (within 10 amino acids from the c-terminal) in its molecule (Y. Kobayashi et al., J. Biochem., 100, 727, 1986), and various amino terminal-truncated derivatives and variants have been reported (Japanese Unexamined Patent Publication, KOKAI, Nos. 61-181298, 62-258324, 63-5099, 63-8398 and 63-8399). Accordingly, from the viewpoint of control of the process during the production of lymphotoxin, there is also a need to develop accurate and rapid assay methods and assay reagents by which it is possible to separately assay various lymphotoxin variants.

Japanese Unexamined Patent Publications, KOKAI, Nos. 58-16687, 59-84827 and 61-186324 describe methods of purification of natural lymphotoxin obtained by culturing animal cells. Other references, Japanese Unexamined Patent Publications, KOKAI, Nos. 61-56197, 63-3796 and 63-17898, and Japanese Patent Application No. 63-35000 as well as P. W. Gray et al, Nature, 312, 721, 1984, and Bringman, Hybridoma, 6, No. 5, 489, 1987, also disclose purification methods for lymphotoxin.

Among the above-mentioned methods, methods of purification by immuno affinity chromatography using an antibody are described in Japanese Unexamined Patent Publication, KOKAI, No. 61-56197, and reports by P. W. Gray and by Bringman respectively. All of these methods have been created by the same inventors, and use antibodies having the same origin.

Since lymphotoxin exhibits remarkably strong and various physiological actions, there is a desire to obtain specific antibodies directed to an identified recognition site in a lymphotoxin molecule, as a means for the separation, purification and quantitation of lymphotoxin, but lymphotoxins from different animal species have a high homology (Chang - Ben Li, J.Immunol., 138, No. 12, 4496–4501, 1987), and low antigenicity. In particular, the homology of amino acid sequences in the carboxy-terminal side of lymphotoxins, which is essential to lymphotoxin activities, is very high, and therefore, it is difficult to obtain an antibody which recognizes the carboxy-terminal side of lymphotoxin, by using a crude antigen and a conventional immunization method.

Monoclonal antibodies to lymphotoxin are disclosed in Japanese Unexamined Patent Publication, KOKAI, No. 61-56197, and T. S. Bringman, Hybridoma, 6, No. 5, 489-507, 1987, but the antibody obtained in Japanese Unexamined Patent Publication No. 61-56197 is not satisfactorily characterized, and a recognition site in the lymphotoxin molecule for the antibody is not described. According to the report by Bringman, among 13 hybridoma clones, 7 clones secreted antibodies recognizing an amino acid sequence from 7th amino acid THR to 19th amino acid LYS in the amino terminal side of a lymphotoxin molecule shown in FIG. 2. Further Bringman disclosed that antibodies secreted by the above-mentioned hybridoma clones did not react with a polypeptide lacking an amino acid sequence from the first amino acid LEU to the 23th amino acid ALA at the amino terminal of the lymphotoxin molecule.

As mentioned above, it is known that the active site of lymphotoxin is in the carboxy terminal side of the molecule, and various amino terminal truncated derivatives and variants have been reported. The shortest sequences believed to exhibit lymphotoxin activities are those having an amino acid sequence wherein from the first amino acid LEU to the 89th amino acid LYS, or from the first amino acid LEU to the 91th amino acid THR, is deleted (Japanese Unexamined Patent Publication No. 62-258324). It is evident that these amino terminal truncated derivatives and variants of lymphotoxin do not react with the monoclonal antibodies reported by Bringman.

In addition, among 13 clones reported by Bringman et al., although antibodies produced by 6 clones other than the above-mentioned 7 clones were confirmed to be reactive with an amino terminal truncated derivative lacking 23 amino acids at the amino terminal of lymphotoxin, it is not known whether these antibodies react with amino terminal truncated derivatives lacking more than 23 amino acids.

As obvious from the above description, only a limited region in a lymphotoxin molecule can be recognized by antibodies to the lymphotoxin, and a hybridoma cell line which secretes a monoclonal antibody which is reactive with a region other than the above-mentioned amino terminal region of physiologically active lymphotoxin variant, is not known.

The methods of purification of natural lymphotoxin mainly use the properties of glycoside chains attached to the lymphotoxin molecule, but since a recombinant lymphotoxin produced by *Escherichia coli* has no glycoside chains, the recombinant lymphotoxin cannot be purified by a method applicable to the purification of natural lymphotoxin.

The methods described in Japanese Unexamined Patent Publication Nos. 63-3796 and 63-17898 can be used to purify both the natural lymphotoxin and the recombinant lymphotoxin, but these methods cannot provide a highly purified lymphotoxin.

Although a process described in Japanese Patent Application No. 63-35000 can provide pure lymphotoxin, the process comprises a large number of purification steps, and the operation thereof is complicated and cumbersome and produces only a low yield. Further, the production of a large amount of lymphotoxin requires a large purification plant, resulting in high production costs.

The above-mentioned difficulties accompanying the purification and separation of lymphotoxin are resolved by an immunoaffinity chromatography using an antibody specific to lymphotoxin. Nevertheless, although antibodies used in the immunoaffinity chromatography described in Japanese Unexamined Patent Publication No. 61-56197 are specific to human lymphotoxin, a recognition region in the lymphotoxin molecule has not yet been identified. Namely, in affinity chromatography, these antibodies do not reliably bind amino terminal truncated derivatives and variants while maintaining their lymphotoxin activities.

In a popular lymphotoxin assay method, its cytotoxic activity to mouse L Cells is measured (Y. Kobayashi et al, J. Immunol, 122, 791, 1979).

More specifically, first mouse L 929 cells or substrains thereof are coated in wells of a 96 well microtiter plate to a monolayer and maintained, usually for 15 to 20 hours, and then double-diluted test samples, and actinomycin D to a final concentration of 1 tg/ml are added to the wells, and the mixture is incubated at 37° C. for 20 to 24 hours. Next, the medium is discarded and the cells are stained with a 0.5% crystal violet solution in methanol/water 1:4. After a thorough washing, the dye is extracted from the cells with ethanol, and the absorbance of the extract is measured at 550 mm using a microplate reader or the like. One unit of lymphotoxin activity is defined as an amount which kills 50% of the total number of L 929 cells or substrains thereof, and the activity is calculated from the dilution ratio of a sample.

The above-mentioned conventional lymphotoxin assay is disadvantageous in that the assay takes as long as over 20 hours, the reading fluctuates depending on an extent of the growth of L 929 cells, resulting in a nonreproducible result, and since the assay cannot distinguish between lymphotoxin and tumor necrosis factor (TNF or TNF-a) having similar physiological properties, it is difficult to quantitate lymphotoxin in a sample containing both the lymphotoxin and a tumor necrosis factor, such as blood, urine and the like.

As a means for solving the above-mentioned problems, a quantitation of lymphotoxin by an immunological method using a monoclonal antibody to lymphotoxin has been reported (T. S. Bringman and B. B. Aggarwal, Hybridoma, 6, 489, 1987; A. Meager et al., J.Immunol. Meth., 104, 31, 1987). It is appreciated that, by using such a method, the assay time is shortened and an assay of lymphotoxin becomes possible in the presence of the tumor necrosis factor. Nevertheless, as described above, since a monoclonal antibody specific to an amino terminal truncated lymphotoxin having lymphotoxin activities has not been found, even the above-mentioned method cannot reliably detect amino terminal truncated derivatives and variants of lymphotoxin.

Accordingly, an immunological assay method for lymphotoxin and assay kit therefor using monoclonal antibodies which are reactive with various variants of lymphotoxin essentially having lymphotoxin activities and specific to an identified recognition site in the lymphotoxin variant, is required.

SUMMARY OF THE INVENTION

The present invention provides a monoclonal antibody reactive with a C-terminal half of human lymphotoxin, and fragments thereof.

The present invention also provides a hybridoma cell line producing a monoclonal antibody reactive with a C-terminal half of human lymphotoxin.

The present invention further provides a process for a production of a monoclonal antibody reactive with a C-terminal half of human lymphotoxin, comprising the steps of:

culturing the above-mentioned hybridoma in a medium, to secrete the antibody; and recovering the antibody from the culture supernatant.

Still further, the present invention provides a process for a production of a monoclonal antibody reactive with a C-terminal half of human lymphotoxin, comprising the steps of:

inoculating the above-mentioned hybridoma to a mammal;

obtaining ascites from the mammal; and, recovering the monoclonal antibody from the ascites.

The present invention also provides a process for a production of a hybridoma cell line producing a monoclonal antibody reactive with a C-terminal half of human lymphotoxin, comprising the steps of:

immunizing a mammal with a conjugate of zinc and a purified recombinant human lymphotoxin;

obtaining spleen cells from the immunized mammal;

fusing the spleen cells with myeloma cells; and cloning a hybridoma producing the monoclonal antibody.

The present invention still further provides an adsorbant for lymphotoxin comprising a solid carrier and a monoclonal antibody reactive with a C-terminal half of human lymphotoxin or fragment of the antibody, wherein the monoclonal antibody is bonded to the surface of the solid carrier.

The present invention also provides a process for a purification of lymphotoxin comprising the steps of:

contacting a material containing lymphotoxin with the above-mentioned adsorbant to adsorb the lymphotoxin to the adsorbant; and eluting the adsorbed lymphotoxin with an eluent.

The present invention additionally provides an assay method or assay kit for assaying lymphotoxin, using the above-mentioned monoclonal antibody.

BRIEF EXPLANATION OF THE DRAWINGS

FIG. 1 represents an amino acid sequence of lymphotoxin disclosed in claim 1 of Japanese Unexamined Patent Publication (KOKAI) No. 63-8399, wherein an amino acid sequence in a dotted line box A represents a region recognized by antibodies of the present invention; and FIG. 2 represents an amino acid sequence of lymphotoxin disclosed in Nature, 312, 721, 1984, wherein an amino acid sequence in a dotted line box B represents a region corresponding to the entire amino acid sequence shown in FIG. 1.

DESCRIPTION OF THE PREFERRED EMBODIMENT

In the present specification and drawings attached thereto, the three-letter symbols representing amino acids have the following meanings;

| ALA: | Alanine | ARG: | Arginine |
|---|---|---|---|
| ASN: | Asparagine | ASP: | Aspartic acid |
| CYS: | Cysteine | GLN: | Glutamine |
| GLU: | Glutamic acid | GLY: | Glycine |
| HIS: | Histidine | ILE: | Isoleucine |
| LEU: | Leucine | LYS: | Lysine |
| MET: | Methionine | PHE: | Phenylalanine |
| PRO: | Proline | SER: | Serine |
| THR: | Threonine | TRP: | Tryptophan |
| TYR: | Tyrosine | VAL: | Valine |

According to the present invention, to construct hybridoma secreting an antibody specific to lymphotoxin, a mouse is immunized with a lymphotoxin-zinc conjugate prepared by adding zinc to a solution of highly purified recombinant lymphotoxin having, for example, an amino acid sequence represented in FIG. 1, to develop antibodies which neutralize lymphotoxin in serum. Preferably, a final immunization is carried out by directly administering the antigen into a spleen (J. Immunol. Methods, 70, 39–43, 1984) to enhance an immune response, and obtaining splenocytes from the spleen for fusion with the myeloma cells. The hybridoma thus obtained are repeatedly screened by measuring an antibody titer in a culture supernatant of the hybridoma, and cloned to establish hybridoma cell lines secreting a monoclonal antibody specific to lymphotoxin. The recognition site in the lymphotoxin molecule recognized by the resulting monoclonal antibody is determined by a partial enzymatic hydrolysis of the lymphotoxin and a measurement of the reactivity of resulting fragments with the antibodies. The thus obtained monoclonal antibodies, according to the present invention, are those which react with a limited region in lymphotoxin molecule, and therefore, are useful for the isolation and purification, as well as quantitative analysis, of lymphotoxin.

Next, the steps for establishing hybridoma and the production of monoclonal antibodies, are described in detail.

(a) Preparation of antigen

Highly purified lymphotoxin can be obtained by a method described in Japanese Patent Application No. 63-35000, wherein zinc is coordinated to the highly purified lymphotoxin to precipitate an antigen, which is then mixed with Freund's complete or incomplete adjuvant to prepare an immunogen.

Japanese Unexamined Patent Publication No. 61-56197 describes a method of obtaining a neutralizing antibody by administering a product prepared by an adsorption of lymphotoxin to aluminum hydroxide gel for immunization, but when the described method was repeated by the present inventors, it failed to provide a neutralizing antibody.

(b) Preparation of antibody-producing cells

Although any mammal can be immunized, mice and rats are preferable because they are easily handled and require only a small amount of antigen. Moreover, since many kinds of cells of mouse myeloma origin have been established as fusion partner cells, and properly characterized, the use of mice is most preferable.

An immunogen may be administered subcutaneously, intraperitoneally, intravenously, intradermally, intramuscularly, or intrasplenically, but the intraperitoneal or intrasplenic administration is most effective.

The immunization may be carried out by a single administration of an immunogen, or by a repeated administration at appropriate intervals, preferably 1 to 5 weeks. Serum samples from the immunized animal are monitored for a desired antibody titer, and at a stage at which the antibody titer becomes sufficiently high, the animal is used as a source of antibody-producing cells to increase the possibility of obtaining hybridoma which secretes a desired antibody.

For the cell fusion, antibody-producing cells such as spleen cells, lymph node cells or peripheral blood cells, obtained 3 to 5 days after the final immunization, are used.

(c) Preparation of myeloma cells

As myeloma cells, generally, established cells derived from mice, such as an 8-azaguanine resistant mouse myeloma cell cell line P3-X63-Ag8-U1 (P3-U1), P3-NS1-1-Ag4.1(NS-1), SP2/O-Ag14 (SP-2), P3-X63-Ag 8.653 (653), P3-X63-Ag8(X63), or the like can be used. These cell strains are passaged in an appropriate medium such as a D'MEM medium or an RPMI 1640 medium supplemented with 8-azaguanine, and for 3 to 4 days before cell fusion, are cultured in the above-mentioned medium before supplementation with 8-azaguanine.

(d) Cell fusion

For the cell fusion, antibody-producing cells and myeloma cells are separately thoroughly washed with a culture medium, such as the above-mentioned medium or phosphate buffered saline (PBS), and both the antibody-producing cells and myeloma cells are mixed to a cell number ratio of antibody-producing cells and myeloma cells of 4:1 to 10:1, and the mixture is centrifuged. After a supernatant is removed, the precipitated cells are loosened, and while warming to 37° C., 30 to 60% polyethylene glycol as a fusion promoter is added dropwise to the cells while stirring. The polyethylene glycol preferably has an average molecular weight of about 1000 to 6000. Several minutes later, a culture medium is gently added to the mixture, and the cells are properly suspended followed by centrifugation to discard the supernatant. Then, to the precipitated sells are added an HAT medium containing $10^{-6}$ to $10^{-3}$M hypoxanthine, $10^{-8}$ to $10^{-7}$M aminopterin and $10^{-6}$ to $10^{-4}$M thymidine, and the cells are again properly suspended.

(e) Selective growth of hybridoma

The suspension prepared as described above is put into wells of a microtiter plate at a ratio of about $10^5$ to $10^6$ cells/well, and culturing is carried out in a $CO_2$ incubator containing about 5% $CO_2$ in air at 35° C. to 40° C.

Where the 8-azaguanine resistant cell line is used as myeloma cells, all non-fused myeloma cells die in the HAT medium within about 10 days. On the other hand, non-fused antibody-producing cells cannot survive the culturing. Accordingly, all cells which grow after 10 to 14 days from the start of culturing are hybridomas.

A half of the supernatant in a well in which hybridoma has grown is replaced with a fresh HT medium (excluding aminopterin from the HAT medium), followed by culturing for several days. An aliquot of a supernatant is obtained and assayed for an anti-lymphotoxin antibody titer by, for example, an enzymeimmunoassay (EIA).

(f) Cloning

Since the presence of two hybridoma in a well is possible, cloning is carried out to isolate a single hybridoma. Any cloning procedure such as a limiting dilution method depending on probability, a manipulating method using soft agar, a sorting method using a cell sorter, or the like may be used.

For wells in which an anti-lymphotoxin antibody titer is detected, cloning by, for example, a limiting dilution method, is repeated two to four times to obtain hybridoma derived from a single cell.

Hybridoma grown in a well in which an antibody titer is stably detected is selected as an anti-lymphotoxin monoclonal antibody-producing hybridoma cell line.

(g) Preparation of antibody

The anti-lymphotoxin monoclonal antibody-producing hybridoma thus selected is cultured on a large scale to obtain a desired antibody in a supernatant. The monoclonal antibody in the supernatant can be isolated and purified by a conventional procedure such as salting out fractionation using ammonium sulfate, ion exchange chromatography, gel filtration, hydroxy apatite chromatography, protein A affinity chromatography or the like, or a combination thereof.

For the production of a large amount of monoclonal antibody, a mineral oil such as pristane (2, 6, 10, 14-tetramethylpentadecane) is intraperitoneally injected to an animal syngeneic with an animal from which myeloma cells an fusion partner have been derived, and then hybridoma cells are intraperitoneally inoculated to the pristane-treated animal. After 10 to 20 days, the hybridoma forms an ascites tumor, resulting in an accumulation of the antibody in a high concentration in the ascites and serum. The ascites or serum is then obtained, and centrifuged to eliminate the debris, and if necessary, the antibody is purified from the supernatant.

(h) Classification of antibodies

The classification, i.e., determination of the isotype and subclass of the monoclonal antibodies obtained as described above, is carried out as follows.

Here, the Ouchterlony method, enzymeimmunoassay (EIA), radioimmunoassay (RIA), and the like may be used. In the enzymeimmunoassay and radioimmunoassay, a culture supernatant as such can be applied to an antigen-immobilized carrier, and as a second antibody, antibodies to various IgG subclasses can be used. Where a concentration of the monoclonal antibody to be tested is relatively high, the Ouchterlony method is preferable.

(i) Identification of region in lymphotoxin recognized by antibody

For identification of a region in a lymphotoxin molecule recognized by the antibody, purified lymphotoxin is partially enzymatically hydrolyzed, and resulting fragments are allowed to react with a monoclonal antibody to determine the recognition region in the monoclonal antibody molecule. The reactivity of the fragment with the monoclonal antibody can be measured by an enzymeimmunoassay or radioimmunoassay.

According to the above-mentioned steps, a hybridoma secreting an anti-lymphotoxin monoclonal antibody, the antigen-recognition region of which has been identified, is established.

An anti-lymphotoxin monoclonal antibody secreted by the above-mentioned hybridoma can be hydrolyzed with an appropriate enzyme such as papain or pepsin to form a Fab fragment, F(ab')$_2$ fragment and the like. Hereinafter, although monoclonal antibodies are described, the descriptions also apply to fragments thereof.

After the anti-lymphotoxin monoclonal antibody thus prepared is purified, the monoclonal antibody is immobilized on a carrier comprising an insoluble matrix, for example polysaccharides, synthetic polymers, or inorganic materials, to prepare an affinity adsorbent, i.e., antibody-bonded adsorbent. The affinity adsorbent is then filled in a chromatography column to prepare an affinity column. As an activated carrier material, cyanogen bromide-activated Separose 4B (Pharmacia), Affigel 10 (Bio-Rad), Affiprep 10 (Bio-Rad), Formylcellulofine (Seikagaku Kogyo), or the like may be used. The above-mentioned affinity adsorbent is brought into contact with a lymphotoxin-containing material, such as a supernatant of a lymphotoxin-producing animal cell line or hybridoma, or a product prepared by disrupting *E. coli* cells transformed with a lymphotoxin gene, or a product prepared after ammonium sulfate fractionation to adsorb the lymphotoxin to the antibody immobilized on the carrier. Next, the adsorbed lymphotoxin is eluted by an appropriate elution means such as a change of pH, a change of polarity, protein denaturating agent, chaotropic ion or the like. Where the lymphotoxin may be inactivated by an eluate, the eluate should be immediately neutralized or dialyzed.

The lymphotoxin preparation thus obtained will have a purity of at least 80 to 90%. This means that a single purification step provides a remarkable increase of purity. For a further purification of lymphotoxin, means for eliminating a small amount of proteins and antibody released from the antibody-bonded adsorbent, contained in the purified lymphotoxin, may be used. Such means includes, for example, ion-exchange chromatography, gel filtration chromatography, hydrophobic chromatography, metal chelate affinity chromatography and the like. The above-mentioned means can be used alone or in combination to obtain a desired purity.

Using such purification processes, the purification can be simply carried out, a small scale purification plant can be used, and the recovery yield increased.

Note, since the present monoclonal antibodies recognize a region present in an amino acid sequence from the 71th alanine to the 152nd leucine of an amino acid sequence of lymphotoxin shown in FIG. 1, they can react with physiologically active lymphotoxin fragments known at present as the shortest amino-terminal truncated lymphotoxin fragments, i.e., a truncated lymphotoxin wherein an amino acid sequence from the first leucine to the 89th lysine has been deleted in FIG. 2 and a truncated lymphotoxin wherein an amino acid sequence from the first leucine to the 91st threonine has been deleted in FIG. 2 (Japanese Unexamined Patent Publication, KOKAI, No. 62-258324), and therefore, the present monoclonal antibodies are useful for the purification of amino terminal truncated lymphotoxin derivatives.

Moreover, the present invention provides an immunological assay method and a kit therefor comprising at least one monoclonal antibody of the present invention, by which method and reagent it is possible to assay all lymphotoxin derivatives exhibiting lymphotoxin activities.

The present immunoassay includes all conventional immunoassay formats such as radioimmunoassay, enzyme immunoassay, and fluorescent immunoassay. The reaction formats include the competitive technique and noncompetitive technique.

Labeling is carried out by a conventional procedure. Namely, for the radioimmunoassay, a radioisotope such as $^{125}I$ is used; for the enzyme immunoassay, a conventional enzyme such as peroxidase or b-galactosidase is preferably used; and for the fluorescent immunoassay, a conventional chromophore can be used as a marker. These assay methods and modifications thereof are well known in the art.

As the present method of assaying a lymphotoxin, preferably a sandwich method is used wherein a antigen-specific monoclonal antibody or polyclonal antibody as the first antibody is attached to an appropriate insoluble carrier, a lymphotoxin antigen is bonded to this carrier, and then a labeled antibody as the second antibody is brought into contact with the carrier.

In a preferable embodiment of the sandwich method, in the first step, as the first antibody the present monoclonal antibody is attached to a solid carrier, and in the second step, the solid carrier is incubated with a sample containing the lymphotoxin to be assayed. In this step, lymphotoxin in the sample is selectively bonded to a lymphotoxin-specific monoclonal antibody of the present invention attached to the carrier. After a conventional washing step, the solid carrier is incubated with a labeled anti-lymphotoxin antibody as the second antibody. Note, the second antibody is not necessarily the present monoclonal antibody but can be a polyclonal antibody. After removing the reaction mixture and washing the solid carrier, the label immobilized to the solid carrier is measured to determine the amount of lymphotoxin in the sample. Alternatively, the present lymphotoxin-specific monoclonal antibody can be used as the second antibody, while using another anti-lymphotoxin antibody as the first antibody.

Another embodiment of the present assay method includes a modified sandwich method wherein, for example, as the second antibody, a biotinated antibody is added followed by the addition of labeled avidin, and then the immobilized label is measured. In the above-mentioned sandwich method, the polyclonal antibody used as the first or second antibody is preferably that produced by immunizing an animal such as a mouse, guinea pig, rat, rabbit, goat, sheep or horse with lymphotoxin purified to a purity of at least 95%, by a conventional procedure, and by concentrating and purifying the obtained antiserum to obtain an immunoglobulin fraction. In the present assay method, a monoclonal antibody and polyclonal antibody as such, or a corresponding fragment having an immunological specificity, such as an Fab fragment, can be used.

The present invention also relates to an immunoassay reagent kit comprising at least one monoclonal antibody of the present invention. Among reagents necessary for an immunoassay of lymphotoxin, that which most strongly affects the specificity and sensitivity of the assay is the specific antibody. By using the present lymphotoxin-specific monoclonal antibody, various kinds of physiologically active derivatives and variants of lymphotoxin can be reliably detected. The present lymphotoxin-specific monoclonal antibodies as the first antibody may be immobilized on an insoluble carrier such as a 96-well microtiter plate, polystyrene beads, or the like. Alternatively, as the second antibody, they may be labeled with a radioisotope, enzyme or the like. Further, polyclonal antibody used in combination with the present monoclonal antibody can be immobilized to a carrier or labeled with an appropriate label, depending on the assay format used.

The carriers used in the present invention include microtiter plate, polystyrene beads, and the like.

EXAMPLES

The present invention will now be further illustrated by, but is by no means limited to, the following examples.

EXAMPLE 1

Preparation of antigenic protein

Recombinant lymphotoxin was obtained according to a procedure described in Examples 1 and 2 of Japanese Patent Application No. 63-35000. Namely, *Escherichia coli* W3110 transformed with plasmid pDK12 containing a lymphotoxin gene coding for the amino acid sequence shown in FIG. 1 was cultured, and the cultured cells were recovered. The cells were disrupted, nucleic acid was removed, and after ammonium sulfate fractionation, a desired fraction was heated. The heated fraction was subjected to anion exchange chromatography, metal chelate chromatography, and gel filtration chromatography to obtain recombinant lymphotoxin having a purity of at least 95%. Then, 1 mg of lymphotoxin was put into a PBS solution, 5 ml of 10 mM zinc acetate was added to the solution, and the mixture was allowed to stand overnight at 4° C. to form a precipitate. The precipitate was washed three times with PBS to obtain a lymphotoxin-zinc conjugate.

EXAMPLE 2

Preparation of immunized mouse spleen cells

An 8-week old BALB/C female mouse was immunized by intraperitoneal administration of 6 μg of the lymphotoxin-zinc conjugate obtained/in Example 1 with Freund's complete adjuvant (FCA). After 4 weeks, the mouse was boosted by intraperitoneal administration of 7 tg of the above-mentioned antigen with Freund's incomplete adjuvant (FIA), and then 3 weeks later, the mouse was boosted with the antigen without adjuvant. One week later, the mouse was finally boosted by directly injecting the antigen without adjuvant into the spleen. Then, 3 days after the final boosting, the spleen was aseptically removed from the mouse to prepare spleen cells for cell fusion.

An antibody titer of serum from the immunized mouse was assayed by enzyme immunoassay (EIA) after the third immunization.

EIA

The EIA was carried out as follows. First, 100 µl/well of a specific antigen diluted in 50 mM carbonate buffer (pH 9.5) (lymphotoxin 3 µg/ml) was distributed to wells of a 96-well EIA plate (#3915; Falcon), and the plate was incubated for two hours at a room temperature, or overnight at 4° C., to coat the antigen on the plate. Protein-binding residues, present on the bottom surface of the plate were saturated by adding 1% bovine serum albumin (BSA) dissolved in PBS and incubating at room temperature for 30 minutes, to prevent a nonspecific adsorption of proteins.

To the antigen-coated plate thus prepared, was distributed 100 µl/well of a stepwise diluted sample (mouse serum, hybridoma culture supernatant, or the like) as the first antibody, and the plate was incubated at room temperature for one hour. After washing three times with PBS containing 0.05% Tween 20 (Bio-Rad) (PBS-Tween), distributed to the plate was 100 µl/well of peroxidase-labeled goat anti-mouse immunoglobulin antibody (DAKO) diluted 1000-fold with PBS as the second antibody, and the plate was incubated at room temperature for one hour. After washing three times with PBS-Tween, 100 µl/well of a peroxidase substrate solution (0.1M citrate buffer, pH 5.0, containing 30 mM o-phenylenediamine and 0.02% hydrogen peroxide) was distributed to the plate, and the plate was incubated at room temperature for 30 minutes. Then, 100 µl of 1.5N sulfuric acid was added to each well as a terminator, and the color formation was determined by measuring the absorbance at 492 nm and 630 by a microplate reader (Bio-Rad).

EXAMPLE 3

Cell fusion

The spleen cells obtained in Example 2 were thoroughly washed with RPMI 1640 (Nissui Seiyaku, Japan), then 8-azaguanine resistant mouse myeloma cells P3-X63-Ag8.653 were similarly thoroughly washed with RPMI 1640, the spleen cells and the myeloma cells were mixed at a ratio of 10:1 of spleen cells to myeloma cells ($1.5 \times 10^8 : 1.5 \times 10^7$), and the mixture was centrifuged at 1000 rpm for 5 minutes. The precipitated cells were slackened, and 1 ml of 50% polyethylene glycol 4000 (PEG 4000; Wako Pure Chemical, Japan) to the cells was added gradually at 37° C. while stirring, and after one minute, the addition of RPMI 1640 was started and continued at a rate of 1 ml/minute while stirring until the total volume of the mixture reached 10 ml. The cells were thoroughly suspended to disrupt cell blocks, and the suspension was centrifuged at 1000 rpm for 5 minutes to discard the supernatant. To the cell precipitate was added 50 ml of HAT medium (RPMI 1640 medium containing 10% fetal calf serum (FCS), supplemented with $10^{-4}$M hypoxanthine, $4 \times 10^{-7}$M aminopterin and $1.5 \times 10^{-5}$M thymidine), and the cells were resuspended. Then 0.1 ml of the cell suspension was distributed to each well of a microplate (#3072; Falcon), and culturing started in a $CO_2$ incubator in a atmosphere of 5% $CO_2$ and 95% air. Next day, 0.1 ml of the HAT medium was added to each well, and a half of the medium was replaced with a fresh HAT medium every 3 to 4 days. The growth of hybridoma was observed from the seventh day. From the tenth day, the fresh medium for the replacement was changed from the HAT medium to an HT medium (HAT medium excluding aminopterin), and by the 16th day, among 518 wells hybridomas were developed in 118 wells. An aliquot of supernatant was taken from each of the 118 wells, and screened for a desired antibody titer by the EIA described in Example 2.

As a result of the first screening, 6 wells of the 118 wells showed a secretion of a specific antibody.

EXAMPLE 4

Cloning of cells producing anti-lymphotoxin monoclonal antibody

For 5 strains among the 6 strains obtained in Example 3, cloning by limiting dilution was carried out by suspending the cells in an RPMI 1640 medium containing 10% FCS at a density of 1 cell/ml, and by distributing 200 µl of the suspension to each well of a microplate (#3072; Falcon). As feeder cells, $1 \times 10^6$ thymus gland cells of a syngeneic mouse were added to each well.

At the 14th day, 39 hybridomas were developed from 480 wells. The antibody titer of a supernatant of each clone was measured by EIA as described in Example 2, and from among the obtained clones, the results for three clones, i.e., hybridoma 1-6-35, hybridoma 1-45-10, and hybridoma 1-74-54, are shown in Table 1.

EXAMPLE 5

Analysis of the number of chromosomes of hybridoma

To the culture media of myeloma cell P3-X63-Ag8.653 described in Example 3 and three hybridomas obtained in Example 4, was added Colcemid (Nakarai Kagaku, Japan) to a final concentration of 0.06 µg/ml and the mixtures were allowed to stand in an atmosphere of 5% $CO_2$ at 37° C. for 4 hours, and then centrifuged to recover the cells. To the cell precipitate, was added 10 ml of 1% sodium citrate for hypotonic treatment. The cells were recovered by centrifugation, fixed to a slide glass with a fixing solution (glacial acetic acid and ethanol 1:3), stained with Giemsa solution, and the number of chromosomes was microscopically counted. The results are shown in Table 1.

EXAMPLE 6

Classification of monoclonal antibody

Culture supernatants of three hybridomas obtained in Example 4 were analyzed by the Ouchterlony method using a monoclonal typing kit (Miles). The subclass of the antibody secreted by each hybridoma clone is shown in Table 1.

TABLE 1

| Clone | Number of chromosomes | Antibody subclass | EIA titer[*] |
|---|---|---|---|
| Myeloma cell P3-X63-Ag8.653 | 52.1 ± 1.71 | — | — |
| Hybridoma 1-6-35 | 86.3 ± 3.36 | IgG$_3$ | 256 |
| Hybridoma 1-45-10 | 84.0 ± 3.81 | IgG$_1$ | 2048 |

TABLE 1-continued

| Clone | Number of chromosomes | Antibody subclass | EIA titer(*) |
|---|---|---|---|
| Hybridoma 1-74-54 | 82.4 ± 2.27 | IgG$_1$ | 2048 |

(*)EIA titer is expressed by a dilution ratio of sample which provides a value of 1.0 of OD 492/630; and a higher EIA titer means a higher content of a specific antibody in a sample.

EXAMPLE 7

Reactivity of monoclonal antibody with lymphotoxin derived from cultured cells

The present inventors have already established a T-cell hybridoma (A-C5-8) secreting lymphotoxin by human T-cell fusion (Japanese Examined Patent Publication, KOKOKU, No. 60-11889; U.S. Pat. No. 1,364,264).

The A-C5-8 strain was stimulated at a cell density of 2×10$^6$ cells/ml with 10 μg/ml concanavalin A (Con A) and 20 ng/ml phorbol myristate acetate (PMA), and cultured for 4 days to recover a culture supernatant. Lymphotoxin in the supernatant was purified according to the Asada et al. method (the 14th Proceedings of Japanese Society for Immunology, page 369, 1984). Namely the supernatant was subjected to 60% saturation ammonium sulfate fractionation, anion exchange chromatography (DEAE-Sephacel), hydrophobic chromatography (phenyl Sepharose), affinity chromatography (lentil lectin Sepharose), and gel filtration chromatography (TSKG 3000 SW), to purify the lymphotoxin.

The obtained lymphotoxin preparation derived from T-cell hybridoma was adjusted to a protein concentration of 30 μg/ml using a 50 mM carbonate buffer (pH 9.5), and 100 tl of the lymphotoxin solution was distributed to each well of a 96 well EIA plate (#3915; Falcon). The plate was incubated at 4° C. overnight to coat the lymphotoxin antigen on the plate. Next, the reactivity of the coated lymphotoxin with culture supernatants of the above-mentioned three hybridoma clones was tested. The results are shown in Table 2.

TABLE 2

| Clone | EIA titer(*) |
|---|---|
| Myeloma cell P3-X63-Ag8.653 | — |
| Hybridoma 1-6-35 | 128 |
| Hybridoma 1-45-10 | 512 |
| Hybridoma 1-74-54 | 512 |

(*)EIA titer is expressed by a dilution ratio of sample which provides a value of 1.0 of OD 492/630.

EXAMPLE 8

Neutralization of lymphotoxin activity by monoclonal antibody

A culture supernatant of each hybridoma obtained in Example 4 was mixed with a same volume of a lymphotoxin solution (100 U/ml), and the mixture was allowed to react at 37° C. for 60 minutes. Then 100 μl/well of the reaction mixture was added to wells of a microplate (#3072; Falcon) in which 1×10$^4$ L.P3 cells (obtained from Tokyo University), a substrain of the L929 cell line, have been grown, and the cells were cultured in the presence of actinomycin D in an atmosphere of 5% CO$_2$, at 37° C. for 18 hours. The surviving cells were stained with 0.5% crystal violet, the crystal violet was extracted from the stained cells with ethanol, and the absorbance of the extract was measured at 550 nm.

One unit of lymphotoxin activity is defined as an amount which provides a 50% fatality rate of L.P3 cells, and an activity in a sample was calculated from the dilution ratio of the sample.

The results of the lymphotoxin neutralizing activity of the culture supernatant of each hybridoma are shown in Table 3.

TABLE 3

| Clone | lymphotoxin activity (U/ml) |
|---|---|
| Medium RPMI-1640/ 10% (FCS) | 100 |
| Myeloma cell P3-X63-Ag8.653 | 100 |
| Hybridoma 1-6-35 | <5 |
| Hybridoma 1-45-10 | 100 |
| Hybridoma 1-74-54 | 10 |

There were difference in neutralization of lymphotoxin activity among the clones.

EXAMPLE 9

Neutralization of TNF by monoclonal antibody

A culture supernatant of each hybridoma clone obtained in Example 4 was mixed with a same volume of 100 U/ml human recombinant tumor necrosis factor (TNF) (Genzyme Corp.), and the mixture was allowed to react at 37° C. for 60 minutes. Next, the same procedure as described in Example 8 were repeated to assay the TNF activity. The results of the TNF neutralization activity of the culture supernatant from hybridoma clones are shown in Table 4.

TABLE 4

| Clone | TNF activity (U/ml) |
|---|---|
| Medium RPMI-1640/ 10% (FCS) | 100 |
| Myeloma cell P3-X63-Ag8.653 | 100 |
| Hybridoma 1-6-35 | 100 |
| Hybridoma 1-45-10 | 100 |
| Hybridoma 1-74-54 | 100 |

As seen from Table 4, the present monoclonal antibody does not neutralize TNF.

EXAMPLE 10

Intraperitoneal growth of hybridoma

First, 0.5 ml of pristane was intraperitoneally administered to 8-week old BALB/C female mice, and 10 days later, 5×10$^6$ cells of the hybridoma clones obtained in Example 4 were intraperitoneally inoculated to the mice. Then, 10 to 20 days later, from mice having abdomens expanded due to an accumulation of the ascites, the ascites were recovered by a syringe and put into a tube containing an anticoagulant. The ascites were recovered at an amount of 2 to 10 ml/time/mouse. The ascites were centrifuged to eliminate cell debris.

An antibody titer of the ascites from the mice inoculated with hybridoma cells was assayed by the EIA as described in Example 2. The results are shown in Table 5.

TABLE 5

| Clone | EIA titer(*) |
|---|---|
| Hybridoma 1-6-35 | $10^5$ |
| Hybridoma 1-45-10 | $10^5$ |
| Hybridoma 1-74-54 | $10^5$ |

(*)The EIA titer is expressed by a dilution ratio of a sample providing a value of 1.0 of OD 492/630.

EXAMPLE 11

Identification of region in antigen recognized by monoclonal antibody

First, 2.4 mg of lymphotoxin obtained in Example 1 was reacted with 100 μl of arginyl endopeptidase solution (Takara Shuzo, Japan) at 35° C. for 18 hours, and the reaction mixture was subjected to reversed phase chromatography wherein the reaction mixture was adsorbed to a silica C4 column AP-803 (4.6×250 mm) (Yamamure Kagaku), and eluted by an acetonitrile linear gradient in the presence of 0.1% trifluoroacetic acid. Fractions of the elute corresponding to peaks were obtained, and after the solvent was removed from the fraction by a centrifugal evaporator, the residue was redissolved in PBS, and fixed on a microplate (#3915; Folcon) which had been treated with 0.2% glutaraldehyde. The reactivity of the polypeptide fragment thus prepared, derived from the arginyl endopeptidase-digestion of lymphotoxin, with a monoclonal antibody secreted by hybridoma 1-74-54, was measured according to the EIA described in Example 2.

The amino acid sequence of a polypeptide which reacted with the antibody in the EIA was determined using a pulse liquid protein sequencer (Applied Biosystems). An amino-terminal amino acid sequence from the first amino acid to the twentieth amino acid of the EIA-positive polypeptide fragment was as follows: ALA-THR-SER-SER-PRO-LEU-TYR-LEU-ALA-HIS-GLU-VAL-GLN-LEU-PHE-SER-SER-GLN-TYR-PRO. From the C4 reversed phase chromatography pattern and the amino acid sequencing, it was found that the monoclonal antibody secreted by hybridoma 1-74-54 recognized an amino acid sequence from the 71th amino acid (ALA) to the 152th amino acid (LEU); namely, the dotted-line-boxed amino acid sequence, in the lymphotoxin amino acid sequence shown in FIG. 1. From a similar analysis, it was confirmed that both the antibody secreted by hybridoma 1-6-35 and the antibody secreted by hybridoma 1-45-10 recognized the same region as that recognizing by the antibody secreted by hybridoma 1-74-54.

EXAMPLE 12

Preparation of antibody-bonded adsorbent

First, 20 ml of the ascites obtained in Example 10 were subjected to 50% saturation ammonium sulfate fractionation, the precipitate was dialyzed against a 0.1M Tris-HCl (pH 7.4) buffer, and the dialyzate was applied to a DEAE-cellulose (DE52: Whatman) column (16×250 mm) previously equilibrated with the same buffer, and a flow-through fraction was recovered as an antibody fraction (IgG fraction) to obtain about 220 mg of IgG. Due to this purification process, the purity of the antibody was at least 90% when determined by electrophoresis.

The IgG fraction thus prepared was bonded to Affiprep 10 (Bio-Rad) to prepare an antibody-bonded adsorbent. Namely, Affiprep 10 was washed on a glass filter with isopropanol while ice-cooling, further washed with ice-water, and the gel recovered.

Then 5 ml of the gel was mixed with 5 ml of 0.2M NaHCO$_3$ (pH 8.3)—0.3M NaCl solution containing 50 mg of the above-mentioned IgG fraction, and the mixture was stirred to allow the bonding reaction. After the reaction, the gel was recovered, washed twice with a mixture of 0.1M NaHCO$_3$ and 0.15M NaCl, and thoroughly mixed with 0.1M ethanolamine hydrochloride (pH 8) to obtain an antibody-bonded adsorbent.

This gel was filled in a column to prepare an antibody-bonded column (10×60 mm).

EXAMPLE 13

Purification of recombinant lymphotoxin

*Escherichia coli* W3100 transformed with plasmid pDK12 containing a lymphotoxin gene was cultured, and the cultured cells were harvested and disrupted. The disruptant was then subjected to nucleic acid-elimination treatment and ammonium sulfate fractionation to prepare a crude product. The crude solution was applied to the antibody-bonded column prepared in Example 12 to adsorb lymphotoxin. After thoroughly washing the column with a 0.02M borate buffer (pH 8.0), the lymphotoxin adsorbed to the column was eluted with a 0.2M glycine-HCl (pH 2.5) buffer. The elute thus obtained was immediately neutralized with a same volume of 0.2M phosphate buffer (pH 7.4) to prevent an inactivation of the lymphotoxin.

The activity of the crude solution was compared with that of the column-treated purified solution. The amount of protein was determined using a protein assay kit (Bio-Rad), and the specific activity, i.e., lymphotoxin activity per 1 mg protein, was calculated. The results of the purification are shown in Table 6.

TABLE 6

| | Total activity (U) | Specific activity (U/mg) |
|---|---|---|
| Crude product | $1.9 \times 10^7$ (100)(*) | $3.2 \times 10^6$ |
| Product purified by antibody-bonded column | $1.5 \times 10^7$ (79)(*) | $2.7 \times 10^7$ |

(*)Parenthesized value shows recovery ratio (%).

As seen from Table 6, by using a monoclonal antibody-bonded column, the lymphotoxin preparation was purified about 10-fold with a high recovery.

EXAMPLE 14

Further purification of lymphotoxin using other column[1]

The high purity lymphotoxin purified by the antibody-bonded column was further purified with DEAE-cellulose (A-500; Seikagaku Kogyo, Japan). Namely, the high purity lymphotoxin purified by the antibody-bonded column was applied to a A-500 column (13×150 mm) previously equilibrated with 10 mM Tris-HCl (pH 8.0) buffer containing 10 mM NaCl, and after thoroughly washing the column with the same buffer, lymphotoxin adsorbed to the column was eluted with 10 mM Tris-HCl (pH 8.0) buffer containing 50 mM NaCl. The lymphotoxin preparation thus obtained was analyzed by sodium dodecylsulfate-polyacrylamide gel electrophoresis (SDS-PAGE) and revealed a purity of more than 99%.

The lymphotoxin activity and specific activity were determined by the same procedure as described above, and the results are shown in Table 7.

TABLE 7

|  | Total activity (U) | Specific acitivity (U/mg) |
|---|---|---|
| Product purified by antibody-bonded column | $4.0 \times 10^7$ (100) | $2.7 \times 10^7$ |
| Product purified by A-500 | $2.9 \times 10^7$ (73) | $3.1 \times 10^7$ |

EXAMPLE 15

Further purification of lymphotoxin using other columns (2)

The high purity lymphotoxin purified using the antibody-bonded column was further purified by metal chelate chromatography and gel filtration chromatography. Namely, the high purity lymphotoxin purified using the antibody-bonded column was applied to a zinc-bonded chelating Sepharose FF column (10×60 mm Pharmacia) previously equilibrated with 20 mM phosphate buffer (pH 7.6) containing 1M NaCl, and after washing the column with the same buffer, lymphotoxin adsorbed to the column was eluted by the same buffer containing 50 mM imidazol.

The elute was further gel-filtrated on a Sephacryl S-200HR (Pharmacia) column (16×1000 mm) to eliminate endotoxin and imidazol. It was confirmed that the resulting lymphotoxin has purity of at least 99%, by SDS-PAGE analysis, and contained endotoxin in an amount of 0.03 ng/mg lymphotoxin, by the toxicolor system (Seikagaku Kogyo, Japan).

The lymphotoxin activity and specific activity were determined by the same procedure as described in Example 13, and the results are shown in Table 8.

TABLE 8

|  | Total activity (U) | Specific activity (U/mg) |
|---|---|---|
| Product purified by antibody-bonded column | $4.0 \times 10^7$ (100) | $2.7 \times 10^7$ |
| Product purified by Zinc chelate and gel filtration | $2.6 \times 10^7$ (65) | $3.1 \times 10^7$ |

EXAMPLE 16

Purification of amino-terminal truncated lymphotoxin

First, 0.8 mg of the high purity lymphotoxin obtained in Example 15 was reacted with 30 μg of arginyl endopeptidase (Takara Shuzo, Japan) at 35° C. for 18 hours, and the reaction mixture was applied to the antibody-bonded column prepared in Example 12. After thoroughly washing the column with a 0.2M borate buffer (pH 8.0), the adsorbed peptide fragments were eluted with a 0.2M glycine-HCl (pH 2.5) buffer. A fraction of the elute containing peptides adsorbed to the column was subjected to reversed phase chromatography, wherein the fraction was applied to a silica C4 column AP-803 (4.6×250 mm; Yamamura Kagaku), and elution was carried out by an acetonitrile linear gradient in the presence of 0.1% trifluoroacetic acid (TFA). Two peaks were found at an acetonitrile concentration of 43% and 45% respectively. Each peak was fractionated, and sequenced using a pulse liquid protein sequencer 477A (Applied Biosystems), and as a result, it was found that the peak eluted at 43% acetonitrile represents a polypeptide having an amino acid sequence from the 71st amino acid (ALA) to the 152nd amino acid (LEU), i.e., the dotted line-boxed amino acid sequence in the lymphotoxin sequence shown in FIG. 1, and the peak eluted at 45% acetonitrile represents not-cleaved (full length) lymphotoxin of a amino acid sequence from the first amino acid (MET) to the 152nd amino acid (LEU) shown in FIG. 1. From the above, it was confirmed that both the polypeptide of from the 71st amino acid (ALA) to the 152nd amino acid (LEU) and the full length lymphotoxin are adsorbed to the antibody-bonded column.

EXAMPLE 17

Reactivity of monoclonal antibody with lymphotoxin derived from cultured cells

The human T-cell hybridoma (A-C5-8) described in Example 7 was stimulated at a cell density of $2 \times 10^6$ cells/ml with 10 μg/ml concanavalin A (Con A) and 20 ng/ml phorbol myristate acetate (PMA), and 4 days later, a culture supernatant was harvested.

Then 10 of the supernatant was applied to the antibody-bonded column prepared in Example 12 to adsorb lymphotoxin, and after thoroughly washing the column with a 0.02M borate buffer (pH 8.0), lymphotoxin adsorbed to the column was eluted with a 0.2M glycine-HCl (pH 2.5) buffer. The obtained eluate was immediately neutralized with the same volume of a 0.2M phosphate buffer (pH 7.4) to prevent an inactivation of the lymphotoxin.

The lymphotoxin activity and specific activity were determined by the same procedure as described in Example 13, and the results are shown in Table 9.

TABLE 9

|  | Total activity (U) | Specific activity (U/gm) |
|---|---|---|
| Culture supernatant | $7.5 \times 10^6$ (100) | $1.5 \times 10^4$ |
| Product purified by antibody-bonded column | $4.1 \times 10^6$ (55) | $2.4 \times 10^7$ |

EXAMPLE 18

Preparation of EIA reagents (1) Preparation of lymphotoxin-specific monoclonal antibody-immobilized plate First, 5 ml of the ascites obtained in Example 10 was adsorbed to a hydroxyapatite (Bio-Rad) column (3 cm×20 cm) previously equilibrated with a 0.01M sodium phosphate buffer (pH 6.8), and eluted with a gradient of a 0.01M to 0.3M sodium phosphate buffer (pH 6.8) to obtain an immunoglobulin (Ig) fraction. The fraction was dialyzed against a 0.2M carbonate buffer (pH 9.5) and the Ig concentration was adjusted to 30 tg/ml with the same buffer. Then 0.2 ml of the solution thus prepared was put into each well of a 96-well microplate (Nunc), and the plate was incubated at 4° C. for 20 hours to coat the Ig on the plate.

Next, the wells of the microtiter plate were washed once with PBS containing 0.05% Tween 20, and twice with PBS, and 0.1 ml of PBS containing 0.5% bovine serum alubumin (BSA) was added to each well to block protein-bonding groups on the plastic surface of the plate with the BSA. The plate thus prepared can be stored in a refrigerator for a long time.

(2) Preparation of anti-lymphotoxin polyclonal antibody

First, 0.3 mg or 1 mg of recombinant lymphotoxin having an amino acid sequence shown in FIG. 1, prepared by a process described in Examples 7 and 8 of Japanese Unexamined Patent Publication (KOKAI) No. 63-8399, was subcutaneously injected with Freund's complete adjuvant to a male rabbit of 2 kg body weight (New Zealand White, Sato Yokei, Japan), and two weeks later, 0.1 mg or 0.4 mg of the same lymphotoxin was subcutaneously injected with Freund's incomplete adjuvant. Two weeks later, 0.03 mg or 0.3 mg of the same lymphotoxin dissolved in PBS was intravenously injected, and a further 10 days later, 0.03 mg or 0.3 mg of the same lymphotoxin was intraveneously injected. After 10 days from the last injection, blood was obtained.

After coagulation, serum was separated from the blood and salted out at a 33% ammonium sulfate saturation and 50% ammonium sulfate saturation. The precipitated fraction was dialyzed against PBS, and centrifuged to obtain a supernatant as an anti-lymphotoxin polyclonal antibody.

The antibody titer of the anti-lymphotoxin polyclonal antibody was $10^6$ to $10^7$ as determined by the EIA method described in Example 2 using as the second antibody a peroxidase-labeled anti-rabbit immunoglobulin goat antibody (DAKO).

(3) Preparation of peroxidase-labeled anti-lymphotoxin polyclonal antibody

First, 0.2 ml of 0.1M $NaIO_4$ was added to 4 mg/ml peroxidase (Sigma), and the mixture was incubated at a room temperature for 20 minutes and dialyzed against a 1 mM acetate buffer (pH 4) followed by a 0.2M carbonate buffer (pH 9.5). The dialyzate was mixed with an anti-lymphotoxin polyclonal antibody, and then incubated at a room temperature for two hours. To the mixture was added 0.4 mg of $NaBH_4$ to carry out a reducing reaction at 4° C. for two hours. The reaction mixture was dialyzed against PBS for 40 hours to obtain an peroxidase-labeled anti-lymphotoxin polyclonal antibody.

(4) Preparation of substrate A

Here, 16 mg of o-pheny-lenediamine (Tokyo Kasei Kogyo, Japan) was distributed to 10 ml vials.

(5) Preparation of substrate B

Here, 30% hydrogen peroxide (Wako Pure Chemical, Japan) was diluted with a 0.1M citrate buffer (pH 5.0) to 0.02% hydrogen peroxide.

EXAMPLE 19

Assay of lymphotoxin

A buffer solution filling the wells of the lymphotoxin-specific monoclonal antibody-immobilized plate prepared in Example 18 (1) was discarded, and then 100 μl of a test sample obtained in Example 14 (containing 10 to 300 U/ml lymphotoxin as determined by a conventional lymphotoxin assay using L.P 3 cells, i.e., a substrain of L 929; specific activity of lymphotoxin: $3 \times 10^7$ U/mg) was added to the wells of the plate. After incubation at 37° C. for 60 minutes, the wells were washed three times with PBS(−) containing 0.05% Tween 20 (washing solution), and to each well was added 100 μl of the labeled antibody prepared in Example 18 (3), which had been 10-fold diluted with the above-mentioned washing solution. After a reaction at 37° C. for 60 minutes, the wells were washed three times with the washing solution. Next, one vial of the substrate A prepared in Example 18(4) was dissolved in 4 ml of the substrate B prepared in Example 18(5), and 100 μl of the solution was added to each well. After terminating the reaction by 1.5N sulfuric acid, the absorbance at 492 nm and 630 nm (main wave length =492 mm) was measured. As a reference, a human TNF α (Genzyme Corp.) was assayed in the same manner. The results are shown in Table 10.

TABLE 10

| Enzyme immunoassay of lymphotoxin | | | |
|---|---|---|---|
| Test sample Lymphotoxin (U/ml) | $OD_{492}-OD_{630}$ | Test sample TNF-a (U/ml) | $OD_{492}-OD_{630}$ |
| 0 | 0.054 | 0 | 0.016 |
| 1 | 0.084 | 1 | 0.037 |
| 3 | 0.132 | 3 | 0.037 |
| 10 | 0.290 | 10 | 0.032 |
| 30 | 0.648 | 30 | 0.031 |
| 100 | 1.341 | 100 | 0.035 |
| 300 | 1.820 | 300 | 0.033 |

As seen from Table 10, the present monoclonal antibody can be used for the assay of lymphotoxin, distinguishing same from TNF-a.

EXAMPLE 20

Two lymphotoxins having different N-terminal amino acid sequence, i.e., the lymphotoxin described in claim 1 of Japanese Unexamined Patent Publication (KOKAI) No. 63-8398 and the lymphotoxin described in claim 1 of Japanese Patent Application No. 62-160115; a culture supernatant of a human T-cell hybridoma (A-C5-8) prepared as described in Example 17; a peptide I having an amino acid sequence from the first amino acid (MET) to the 70th amino acid (LYS) in the amino acid sequence shown in FIG. 1, and a peptide I having an amino acid sequence from the 71st amino acid (ALA) to the 152nd amino acid (LEU) in the amino acid sequence shown in FIG. 1 both prepared by cleaving the lymphotoxin shown in FIG. 1 and separating the resulting peptide fragments by C4 reversed phase chromatography, were assayed for lymphotoxin activity by the method described in Example 19.

TABLE 11

| Test sample | conventional assay | $OD_{491}-OD_{630}$ |
|---|---|---|
| Lymphotoxin 63-8398 of J.P.P. | 68 U/ml | 1.052 |
| Lymphotoxin 62-160115 of J.P.A. | 105 U/ml | 1.360 |
| A-C5-8 supernatant | 50 U/ml | 0.920 |
| Peptide I | <4 U/ml | 0.060 |
| Peptide II | <4 U/ml | 1.450 |

(*)Cytotoxity test using L.P3 cells as described in Example 8.

EXAMPLE 21

Preparation of peroxidase-labeled lymphotoxin-specific monoclonal antibody

First, 0.2 ml of 0.1M $NaIO_4$ was added to 4 mg/ml peroxidase, and after the mixture was incubated at room temperature for 20 minutes, the mixture was dialyzed against a 1 mM acetate buffer (pH 4), followed by a 0.2M carbonate buffer (pH 9.5). The dialyzate was mixed with 6 mg of lymphotoxin-specific monoclonal antibody prepared by the method described in Example 18, and the mixture was incubated at room temperature for two hours. Then 0.4 mg of $NaBH_4$ was added to the mixture for to carry out a reducing reaction at 4° C. for 2 hours, and the mixture was dialyzed against PBS for 40 hours to prepare a peroxidase-labeled lymphotoxin-specific monoclonal antibody.

EXAMPLE 22

Assay of lymphotoxin in mouse serum or human serum

Known concentrations of lymphotoxin were added to the serum of BALB/C mouse and to healthy human serum to prepare test samples, which were then assayed by the EIA as described in Example 19. The results are shown in Table 12.

TABLE 12

| Test sample | $OD_{492}-OD_{630}$ | Test sample | $OD_{492}-OD_{630}$ |
|---|---|---|---|
| Lymphotoxin in buffer | | Lymphotoxin in mouse serum | |
| OU/ml | 0.028 | OU/ml | 0.029 |
| 1 | 0.050 | 1 | 0.049 |
| 3 | 0.090 | 3 | 0.084 |
| 10 | 0.203 | 10 | 0.198 |
| 30 | 0.440 | 30 | 0.423 |
| 100 | 0.862 | 100 | 0.873 |
| 300 | 1.326 | 300 | 1.460 |
| | | Lymphotoxin in human serum | |
| | | OU/ml | 0.028 |
| | | 1 | 0.049 |
| | | 3 | 0.087 |
| | | 10 | 0.189 |
| | | 30 | 0.427 |
| | | 100 | 0.887 |
| | | 300 | 1.485 |

These results shows that the presence of serum does not affect the EIA of the present invention, i.e., that the present assay can be applied to an assay of lymphotoxin present in the serum.

Monoclonal antibodies of the present invention specifically react with human lymphotoxin, and therefore, they are useful for a simple and rapid isolation and purification of lymphotoxins from a material containing same. Further, since the present monoclonal antibodies react with the C-terminal half of lymphotoxin, they are useful for the isolation and purification of various kinds of biologically active derivatives and variants of lymphotoxin, and therefore, are promising for an acceleration of studies of various kinds of lymphotoxin derivatives created from protein technology directed to the development of less toxic and highly effective lymphotoxin derivatives.

Moreover, the lymphotoxin assay method and assay kit remarkably reduce the time necessary for the lymphotoxin assay, and can be applied to the assay of lymphotoxins in a sample containing both lymphotoxin and TNF-α, such as a sample from a organism. Moreover, since the present assay method and assay kit detect amino-terminal truncated lymphotoxin derivatives, they can be applied to the assay of various kinds of biologically active lymphotoxin derivatives and variants.

The hybridomas of the present invention were deposited with the Fermentation Research Institute, Agency of Industrial Science and Technology 1-3, Higashi 1-chome Tsukuba-shi Ibaraki-ken, 105, JAPAN, as international depositions under the Budapest treaty on May 24, 1988.

Hybridoma 1-6-35 FERM BP-1890
Hybridoma 1-45-10 FERM BP-1891
Hybridoma 1-74-54 FERM BP-1892.

We claim:

1. A monoclonal antibody produced by a hybridoma selected from the group consisting of hybridoma 1-6-35 (FERM BP-1890), hybridoma 1-45-10 (FERM BP-1891) and hybridoma 1-74-54 (FERM BP-1892), or a specific binding fragment thereof.

2. A monoclonal antibody fragment according to claim 1, selected from the group consisting of Fab, and F(ab)$_2$.

3. A hybridoma cell line selected from the group consisting of hybridoma 1-6-35 (FERM BP-1890), hybridoma 1-45-10 (FERM BP-1891), and hybridoma 1-74-54 (FERM BP-1892).

4. An absorbent for lymphotoxin comprising a solid carrier and a monoclonal antibody produced by a hybridoma selected from the group consisting of hybridoma 1-6-35 (FERM BP-1890), hybridoma 1-45-10 (FERM BP-1891) and hybridoma 1-74-54 (FERM BP-1892), wherein the monoclonal antibody is bonded to the surface of the solid carrier, said solid carrier selected from the group consisting of polysaccharides, synthetic polymers, and inorganic materials.

5. An assay method for lymphotoxin, comprising the steps of:
   (a) preparing a solid carrier on which a first antibody to lymphotoxin has been attached;
   (b) incubating the solid carrier from step (a) with a sample to be assayed;
   (c) incubating the solid carrier from step (b) with a labeled second antibody to lymphotoxin; and
   (d) detecting the label immobilized to the solid carrier,
at least one of the first and second antibodies being a monoclonal antibody or fragment thereof according to claim 3.

6. An assay kit for assaying lymphotoxin, comprising a monoclonal antibody or fragment thereof according to claim 1, the monoclonal antibody or fragment thereof being attached to a solid carrier.

7. An assay kit for assaying lymphotoxin, comprising a first antibody to lymphotoxin and a second antibody to lymphotoxin, at least one of the first and second antibodies being a monoclonal antibody or a fragment thereof according to claim 1.

* * * * *

UNITED STATES PATENT AND TRADEMARK OFFICE
CERTIFICATE OF CORRECTION

PATENT NO. : 5,188,969

DATED : February 23, 1993

INVENTOR(S) : Arai et al.

It is certified that error appears in the above-identified patent and that said Letters Patent is hereby corrected as shown below:

Col. 22, line 54   Delete " claim 3 " and substitute -- claim 1--

Signed and Sealed this

Twenty-second Day of March, 1994

*Attest:*

BRUCE LEHMAN

*Attesting Officer*   *Commissioner of Patents and Trademarks*